(12) United States Patent
Zajarias (10) Patent No.: US 10,307,240 B2
(45) Date of Patent: Jun. 4, 2019

(54) METHODS AND APPARATUS FOR CAPTURING EMBOLIC DEBRIS DURING ENDOVASCULAR PROCEDURES

(71) Applicant: Alan Zajarias, St. Louis, MO (US)

(72) Inventor: Alan Zajarias, St. Louis, MO (US)

(*) Notice: Subject to any disclaimer, the term of this patent is extended or adjusted under 35 U.S.C. 154(b) by 454 days.

(21) Appl. No.: 13/710,676

(22) Filed: Dec. 11, 2012

(65) Prior Publication Data

US 2014/0163603 A1    Jun. 12, 2014

(51) Int. Cl.
*A61F 2/01* (2006.01)
*A61F 2/24* (2006.01)

(52) U.S. Cl.
CPC ............ *A61F 2/013* (2013.01); *A61F 2/2427* (2013.01); *A61F 2230/0067* (2013.01)

(58) Field of Classification Search
CPC ...... A61F 2/01; A61F 2/013; A61F 2002/011; A61F 2002/016; A61F 2230/0067; A61F 2002/015; A61F 2002/018; A61B 17/22; A61B 17/221; A61B 2017/22001; A61B 2017/22002
USPC ......................................................... 606/200
See application file for complete search history.

(56) References Cited

U.S. PATENT DOCUMENTS

| | | | |
|---|---|---|---|
| 5,549,626 A * | 8/1996 | Miller | A61F 2/01 606/191 |
| 5,649,953 A * | 7/1997 | Lefebvre | A61F 2/01 604/104 |
| 5,669,933 A * | 9/1997 | Simon | A61F 2/01 600/191 |
| 5,827,324 A | 10/1998 | Cassell et al. | |
| 5,853,420 A * | 12/1998 | Chevillon et al. | 606/200 |
| 5,941,896 A * | 8/1999 | Kerr | 606/200 |
| 6,090,097 A * | 7/2000 | Barbut et al. | 604/511 |
| 6,152,946 A * | 11/2000 | Broome et al. | 606/200 |
| 6,214,025 B1 * | 4/2001 | Thistle et al. | 606/200 |
| 6,264,672 B1 | 7/2001 | Fisher | |
| 6,361,545 B1 * | 3/2002 | Macoviak | A61B 17/12136 606/151 |
| 6,458,151 B1 * | 10/2002 | Saltiel | A61F 2/013 604/104 |
| 6,589,264 B1 | 7/2003 | Barbut et al. | |

(Continued)

FOREIGN PATENT DOCUMENTS

| | | |
|---|---|---|
| WO | 9839053 A1 | 9/1998 |
| WO | 9847447 A1 | 10/1998 |

*Primary Examiner* — Ryan J. Severson
*Assistant Examiner* — Christian D Knauss
(74) *Attorney, Agent, or Firm* — Armstrong Teasdale LLP (57) ABSTRACT

Methods and apparatus for use in capturing embolic debris during a surgical procedure in a patient are provided. The methods include utilizing an embolic capture device that is configured for delivery into a patient via a transapical delivery approach and via an arterial delivery approach, and determining which of a transapical delivery approach and an arterial delivery approach should be used with the patient. The methods also include inserting the embolic capture device within a delivery system, and deploying the embolic capture device at a desired location within the patient's blood vessel that is downstream from the location of the surgical procedure. The same embolic capture device is configured for use with a transapical delivery approach and an arterial, such as a transfermoral, delivery approach.

17 Claims, 6 Drawing Sheets

(56) References Cited

U.S. PATENT DOCUMENTS

| | | | |
|---|---|---|---|
| 6,592,546 B1 | 7/2003 | Barbut et al. | |
| 6,656,204 B2 | 12/2003 | Ambrisco et al. | |
| 6,656,351 B2 | 12/2003 | Boyle | |
| 6,840,950 B2 | 1/2005 | Stanford et al. | |
| 7,083,633 B2 | 8/2006 | Morrill et al. | |
| 7,229,463 B2* | 6/2007 | Sutton et al. | 606/200 |
| 7,244,267 B2* | 7/2007 | Huter et al. | 606/200 |
| 7,604,612 B2 | 10/2009 | Ressemann et al. | |
| 7,976,560 B2 | 7/2011 | Denison et al. | |
| 8,187,298 B2 | 5/2012 | Pal | |
| 8,236,024 B2 | 8/2012 | Stanford et al. | |
| 8,262,691 B2 | 9/2012 | McGuckin, Jr. et al. | |
| 2003/0097114 A1* | 5/2003 | Ouriel | A61B 17/22 604/500 |
| 2003/0212431 A1* | 11/2003 | Brady et al. | 606/200 |
| 2004/0158274 A1* | 8/2004 | WasDyke | 606/200 |
| 2005/0038470 A1* | 2/2005 | van der Burg et al. | 606/213 |
| 2005/0159771 A1* | 7/2005 | Petersen | 606/200 |
| 2005/0222604 A1* | 10/2005 | Schaeffer | 606/200 |
| 2006/0015136 A1* | 1/2006 | Besselink | A61F 2/013 606/200 |
| 2006/0036279 A1* | 2/2006 | Eidenschink et al. | 606/200 |
| 2007/0088383 A1* | 4/2007 | Pal et al. | 606/200 |
| 2008/0065145 A1* | 3/2008 | Carpenter | 606/200 |
| 2009/0318951 A1* | 12/2009 | Kashkarov | A61F 2/01 606/200 |
| 2010/0030253 A1* | 2/2010 | Harris et al. | 606/200 |
| 2010/0063533 A1* | 3/2010 | Sokolov et al. | 606/200 |
| 2010/0179647 A1* | 7/2010 | Carpenter et al. | 623/2.11 |
| 2010/0211095 A1 | 8/2010 | Carpenter | |
| 2011/0282379 A1* | 11/2011 | Lee | A61F 2/01 606/200 |
| 2012/0179033 A1 | 7/2012 | Merhi | |

* cited by examiner

METHODS AND APPARATUS FOR CAPTURING EMBOLIC DEBRIS DURING ENDOVASCULAR PROCEDURES

BACKGROUND OF THE INVENTION

This invention relates generally to filtering devices, and more particularly, to methods and apparatus for use in capturing emboli within a blood vessel during endovascular surgical procedures.

Recent technology advances have been made in the area of cardiac surgery, including transcatheter valve replacement and repair procedures that may be performed without arresting the heart while systemic circulation is maintained. In some cardiac procedures, blood flow within portions of the heart, and aorta, must be interrupted, while other known procedures require cardiopulmonary bypass (CPB) with cardioplegia. However, technology advances, in areas such as echocardiography and flouroscopy, have enabled surgeons to visualize the cardiovascular system in more detail, and as a result, have enabled cardiac surgical procedures that do not require blood flow occlusion, or cardiopulmonary bypass. Because the patient's blood flow remains uninterrupted during such procedures, there are other inherent potential risks to the patient with such cardiovascular procedures. For example, the risk of stroke or neurologic deficit to the patient may be increased as a result of emboli, plaque, and/or thrombi being undesirably released into the blood stream. Clinical studies have shown that debris that is undesirably dislodged during manipulation of the heart and/or blood vessel may cause a stroke, other neurologic deficit, or infraction, depending upon where the debris travels within the patient's vascular system.

To reduce the likelihood of potential cerebral and/or other peripheral embolic events associated with such surgical procedures, several approaches have been developed to prevent emboli from traveling within the vasculature. For example, in at least some known procedures, a device may be inserted into the vessel in an attempt to deflect the emboli from one portion of the patient's heart, i.e., the carotid arteries, into a different area of the patient, i.e., the descending aorta. However, because such devices do not trap the emboli, a risk of embolisms in other areas of the patient's body remains and as such, such devices may provide only limited benefits.

Other embolic protection approaches include filtering devices that attempt to trap debris flowing through the vasculature. Positioning a filter in the vasculature during treatment can reduce the amount of embolic debris traveling in the bloodstream. Generally, such filters are inserted into the patient, with a containment catheter, in a collapsed state, and are sprung outwardly when released from the containment catheter and when positioned in a desired location within the patient's blood vessel. However, the use of such filters may be limited depending on the condition of the patient's vessels through which such filters are delivered to the treatment site. More specifically, because of their design and operation, some known filters may only be inserted within a patient via the femoral artery (transfemoral) or radial artery. Such devices are generally utilized for capturing embolic debris within saphenous vein graft or carotid stenting. However, because of patient limitations, such as weak or obstructed arteries, for example, some cardiac procedures may not be performed on a patient using a transfemoral approach. In addition, because of the fluidic pressure within the patient's blood vessel, at least some known filters may be difficult to secure in position within the vessel, may be difficult to accurately position within the patient, and/or may be used in only limited positions within the patient, such as within a portion of their aortic arch, for example.

Moreover, depending on the size of the mesh used in fabricating known filters, and depending on the amount of build-up within the patient, known filters may become quickly clogged, may create an unacceptably high pressure drop across the filter, and/or may obstruct the blood flow during the surgical procedure. Furthermore, many known filters are not sized to extend fully across the blood vessel, and as such only filter a portion of the blood downstream from the surgical treatment site, such that debris may either accumulate on external supports of the filter or flow past the filter.

After the surgical procedure is completed, known filters are generally collapsed and removed from the blood vessel. However, depending on the size of the filter and the amount of debris collected, as the filtering device is being collapsed for removal, it is possible for debris that has become stuck to the external supports of the filter to become dislodged and be carried away by the blood stream. Moreover, depending on the complexity of the filtering device, there may be a risk of trapped emboli escaping as the filter is collapsed within the blood vessel for removal from the patient. Accordingly, it would be desirable to provide an improved filtering device that does not obstruct blood flow while in use, that can be delivered to a desired location via a transapical delivery or through another vascular route, including a transfemoral passage, that may be easily positioned and centered within a desired location within a blood vessel, and that has a relatively simple design that provides the surgeon with a positive control of its use.

BRIEF DESCRIPTION OF THE INVENTION

In one aspect, a method of capturing embolic debris during a surgical procedure in a patient is provided. The method includes utilizing a filter that is configured for delivery into a patient via a transapical delivery approach and via a an arterial delivery approach, and determining which of the transapical delivery approach and the arterial delivery approach should be used with the patient. The method also includes inserting a filter within a delivery system, and deploying the filter at a desired location within the patient's blood vessel that is downstream from the location of the surgical procedure.

In another aspect, an embolic protection system is provided. The system includes an embolic capture device and a filter delivery system. The filter is for use in capturing embolic debris entrained within a patient's blood flow in a blood vessel. The filter delivery system is configured to contain said filter therein for delivery to a desired location within a patient. The filter delivery system is configured to deliver the filter to the desired location within the patient via a transapical approach. The filter delivery system is further configured to deliver the filter to the desired location via an arterial approach through the patient. The filter is configured to filter blood flow within the patient without cardiopulmonary bypass.

In another aspect a filter for use in capturing embolic debris entrained in a blood vessel is provided. The filter includes an inlet end, an opposite capture end, and a body extending therebetween. The inlet end includes a first mechanism for use in selectively positioning the filter within a blood vessel at a desired location. The capture end includes a second mechanism for use in selectively positioning the filter within a blood vessel a desired location. The body includes a plurality of pores that are sized to capture embolic debris entrained in blood flowing through the filter. The filter is configured for deployment to the blood vessel through a delivery system via an arterial route. The filter is further configured for deployment to the blood vessel through a delivery system via a tranapical route. The filter is selectively moveable from an expanded state in which the inlet end is substantially circular and has a larger diameter than a diameter of the capture end, to a collapsed state wherein the inlet end is non-circular and is approximately the same size as the diameter of the capture end. The filter body is biased towards its expanded state.

DETAILED DESCRIPTION OF THE INVENTION

Figure 1:
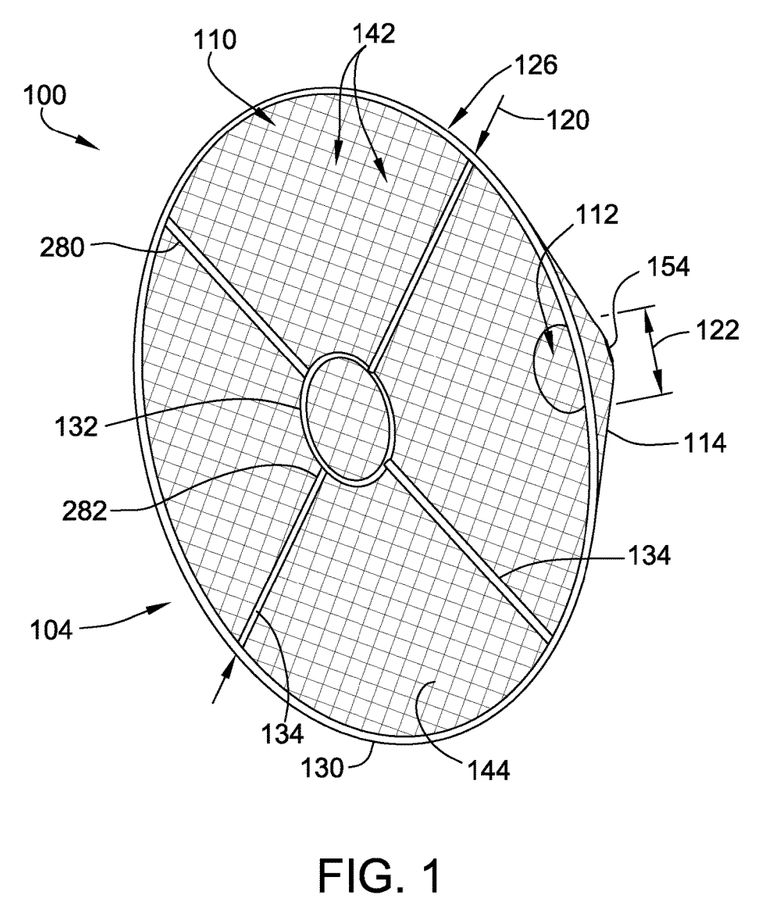
FIG. 1 is a perspective view of an exemplary embolic capture device or filter in an expanded state that may be used in capturing emboli within a blood vessel during endovascular surgery.
Figure 2:
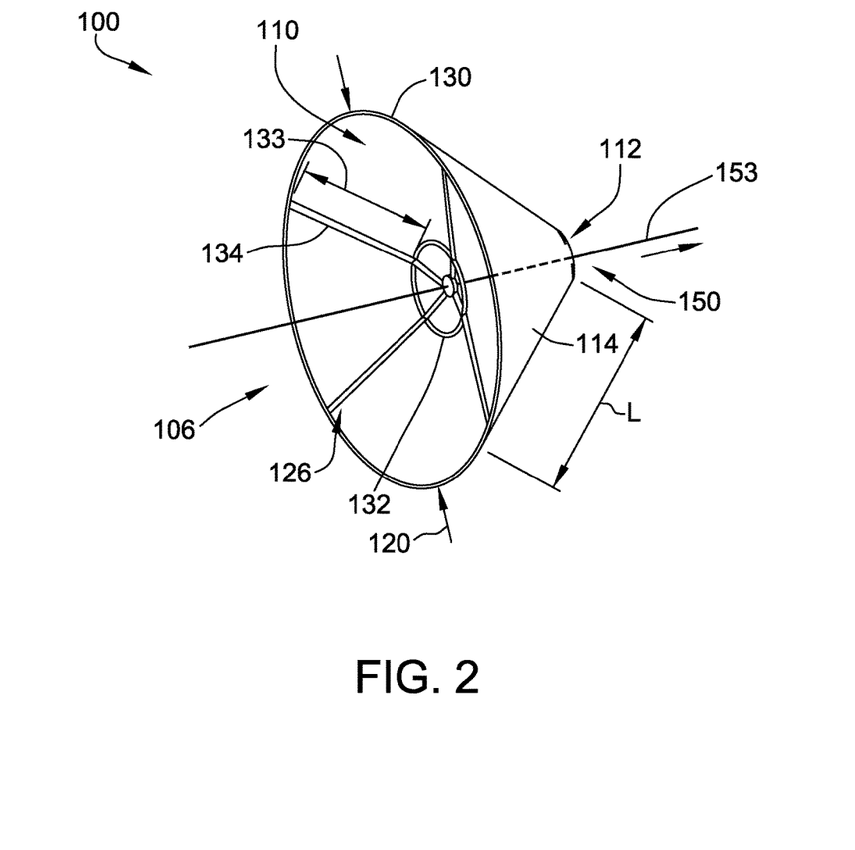
FIG. 2 is a perspective view of the filter shown in FIG. 1 and in a partially collapsed state.

FIG. 1 is a perspective view of an exemplary embolic capture device or filter 100, in an expanded state 104, that may be used in capturing emboli (not shown) within a body or blood vessel (not shown) during an endovascular procedure or surgical procedure. FIG. 2 is a perspective view of filter 100 in a partially collapsed state 106. In the exemplary embodiment, filter 100 is used in support of cardiovascular surgery. As such, in the exemplary embodiment, as used herein, the term "endovascular," refers to surgical procedure(s) that are performed with interventional tools and supporting catheters and other equipment introduced to the heart chambers from the patient's arterial or venous vasculature remote from the heart. The tools and other equipment may be introduced percutaneously, i.e., through an access sheath, or may be introduced via a surgical cut down, and then advanced from the remote access site through the vasculature until they reach the patient's beating heart. Moreover, as will be appreciated by one of ordinary skill in the art, the methods and apparatus described herein are not limited to use only with percutaneous and intravascular techniques, but rather the present invention may be used with open surgical procedures as well. Furthermore, as will be appreciated by one of ordinary skill in the art, the methods and apparatus described herein are not limited to only being used with only cardiovascular surgical procedures.

In the exemplary embodiment, filter 100 is formed with an open end 110, a closed end 112, and a body 114 extending therebetween. Body 114, in the exemplary embodiment, is generally conical (e.g., (e.g., conical, frusto-conical, etc.) such that open end 110 has a larger diameter 120 than a diameter 122 of closed end 112. Diameters 120 and 122 are variably selected depending on the surgical procedure being performed and depending on the desired filtration location within the patient. For example, in one embodiment, filter 100 is sized for insertion within a patient's aorta and as such, diameter 120 is between about 3.8 cm to about 6.5 cm. In each embodiment, open end diameter 120 is sized to enable filter open end 110 to extend across substantially all of an inner diameter (not shown) of a blood vessel (not shown) and substantially circumferentially contact and substantially conform against, an inner wall (not shown) of the blood vessel when deployed at a desired location within a patient.

Filter open end diameter 120 is defined by a filter support structure 126 that provides support to body 114 at open end 110 and that enables filter 100 to be selectively transitioned from deployed state 104 to collapsed state 106. In the exemplary embodiment, filter support structure 126 includes an annular ring 130, a center coupling mechanism 132, and a plurality of struts 134, that work in combination to provide support to body 114 at open end 110 and to provide a means to selectively transition filter 100 from deployed state 104 to collapsed state 106. In one embodiment, ring 130 is formed in a split ring configuration (not shown in FIGS. 1-3) with a coupling mechanism (not shown in FIGS. 1-3) that enables a an operator to selectively adjust a diameter 120 of open end 110 after filter 100 is deployed in a desired location within a blood vessel.

In the exemplary embodiment, filter 100, as described in more detail below is passively deployed and either ring 130 or coupling mechanism 132 is fabricated from any material that enables filter 100 to function as described herein. In an alternative embodiment, filter 100 may be configured to be deployed in an active manner wherein filter 100 is expanded manually using for example, a mechanical actuator and/or by releasing a retaining mechanism designed to maintain filter 100 in a collapsed state 106. More specifically, as described in more detail below, in the exemplary embodiment, filter 100 is deployed passively, but in a manner via a delivery system that facilitates providing enhanced control to the surgeon or operator, as compared to known embolic filtering systems. For example, in the exemplary embodiment, ring 130, coupling mechanism 132, and/or struts 134 are fabricated from a superelastic material or a shaped memory alloy (SMA) material, such as, but not limited to Nitinol®, stainless steel, plastic, or any other alloy that has properties that enables the material to develop a shaped memory effect (SME). In the exemplary embodiment, struts 134 extend substantially radially between coupling mechanism 132 and ring 130. Alternatively, any portion of support structure 126 and/or filter 100 may be fabricated from any material, including a shaped memory alloy material that enables filter 100 to function as described herein.

In the exemplary embodiment, coupling mechanism 132 is substantially circular and filter 100 includes four struts 134. Alternatively, filter 100 may include any other filter support structure that enables filter 100 to function as described herein, and/or that has any other non-circular shape. Moreover, filter 100 may include any number of struts 134 and/or may include any other coupling mechanism that enables filter 100 to function as described herein. For example in some embodiments, struts 134 may be longitudinally compressible or telescoping to enable a distance between ring 130 and coupling mechanism 132 (i.e., a length 133 of each spoke 134) to be selectively varied.

Body 114, in the exemplary embodiment, is coupled to filter support structure 126. More specifically, in the exemplary embodiment, body 114 extends from ring 130 to closed end 112. Moreover, in the exemplary embodiment, body 114 is formed in a screen 144 fabricated from a mesh material that forms a filter pocket. In an alternative embodiment, body 114 may be fabricated from a cloth fabric. For clarity, the mesh material has not been illustrated in FIG. 2. In one embodiment, the mesh material is a woven or knitted fabric, such as a polyester or nylon material that is flexible. In another embodiment, body 114 is fabricated from a nonwoven material, such as spun polyolefin material. In yet another embodiment, body 114 may be fabricated from a combination of materials including textile and/or wire fibers. Alternatively, body 114 may be fabricated from any material, including Nitinol and/or stainless steel, that enables filter 100 to function as described herein. For example, in some embodiments, body 114 may be fabricated from a shaped memory material.

In the exemplary embodiment, body 114 is formed with substantially equi-sized pores or openings 142 that are sized large enough to enable blood to flow therethrough with little obstruction and without creating a pressure differential across filter 100, while being small enough to capture embolic debris of a desired size. As used herein, embolic debris may include any constituent of blood, calcium, or atheromatous material and superimposed thrombus, which may cause complications in the body if allowed to travel freely in the blood stream. Such debris may include, but is not limited to only including, atheromatous fragments, fats, platelets, fibrin, clots, calcium deposits, or gaseous materials. For example, in one embodiment, screen 144 is formed with pores 142 that are between about 50 micrometers to about 200 micrometers. Alternatively, body 114 can be formed with pores 142 of varying sizes and/or may be formed with pores 142 of any size that enables filter 100 to function as described herein. In some embodiments, to enhance the operation of filter 100, body 114 may be coated with an adhesive material that facilitates embolic debris sticking to body 114.

Screen 144 is variably selected and sized to ensure pores 142 are sized large enough to enable blood to flow through filter 100 freely, yet small enough to facilitate capturing embolic debris entrained in the blood flow. More specifically, in each embodiment pores 142 are sized to capture embolic debris without unduly disrupting blood flow and/or without creating a pressure drop across filter 100. In the exemplary embodiment, pores 142 are substantially uniformly sized throughout screen 144. Alternatively, pores 142 can be sized differently within screen 144. Furthermore, in some embodiments, screen 144 may be fabricated using multiple materials and/or using mesh and/or cloth materials that have different textures and/or thread diameters, for example. In addition, any length L of filter 100, as defined between filter open and closed ends 110 and 112, respectively, any pore size 142, and/or any shape of filter 100 may be used that enables filter 100 to function as described herein.

In the exemplary embodiment, filter body 114 is shaped such that when filter 100 is deployed 105, support structure ring 130 is positioned substantially against the blood vessel inner wall, (i.e., an inner wall of the patient's aorta, in the exemplary embodiment) and filter screen 144 tapers away from the blood vessel inner wall. Orienting and tapering screen 144 as such, facilitates ensuring that blood flow through pores 142 remains substantially un-occluded by contact with the blood vessel inner wall. Moreover, in the exemplary embodiment, the shape of filter body 114 facilitates ensuring that blood flow into branches of the aorta is not obstructed by filter 100 during the surgical procedure. In other embodiments, body 114 may have any other shape that enables filter 100 to function as described herein.

In each embodiment, body 114 is highly flexible and is selectively collapsible as described herein. When filter 100 is deployed and is in expanded state 104, struts 134 extend radially inward from ring 130 towards a centerline axis 153 of filter 100. Moreover, when filter 100 is deployed within a blood vessel, filter 100 will be positioned at a desired location within a patient such that open end 110 extends substantially across the blood vessel and is substantially perpendicular to the direction of the blood flow through the blood vessel. More specifically, as described in more detail below, when deployed in the blood vessel, support structure 126 retains filter open end 110 against the inner wall of the blood vessel such that substantially all of the blood flowing downstream from the surgical location through the blood vessel flows through filter 100 and through screen 144.

In the exemplary embodiment, filter 100 is configured to expand to a radially open, expanded configuration 104 when not confined, for example, by being within a delivery system (not shown in FIG. 1). More specifically, in the exemplary embodiment, the shaped memory material used in fabricating at least a portion of filter 100 biases filter 100 towards its deployed and expanded configuration 104. When fully expanded, filter open end 110, in the exemplary embodiment, is substantially circular. In other embodiments, filter open end 110 may have any other cross sectional shape, including elliptical, that enables filter 100 to function as described herein. Moreover, when fully expanded, filter body 114 has a generally tubular configuration that extends from open end 110 to closed end 112.

Closed end 112, in the exemplary embodiment, is substantially circular when filter 100 is in expanded state 104. In other embodiments, filter closed end 112 may have any other cross sectional shape, including elliptical, that enables filter 100 to function as described herein. In the exemplary embodiment, screen 144 extends completely across closed end 112 such that any flow exiting closed end 112 flows through pores 142. In the exemplary embodiment, closed end 112 includes a coupling mechanism 150 that enables filter 100 to be "captured" and that increases the flexibility to a surgeon or operator, as described in more detail below. More specifically, in the exemplary embodiment, coupling mechanism 150 includes a plurality of magnets that are spaced circumferentially about an outer perimeter of closed end 112 that enable filter 100 to couple to a guide wire, a sheath, a deployment tool, and/or any other device that facilitates positioning and/or maintaining a relative position of filter 100 within a blood vessel. In one embodiment, the magnets are electro-magnets that generate a current that enables filter 100 to be selectively positioned in a blood vessel, as described in more detail below, without adversely affecting a pacemaker that may be in the patient. Alternatively, other types of magnets may be used, including rare earth magnets and/or permanent magnets, for example. Furthermore, in other embodiments, filter 100 may not include magnets, but rather a different coupling mechanism may be used to couple filter 100 to a device within the blood vessel, such as, a mechanical handle, a threaded coupling, and/or a loop, for example. Alternatively, any other coupling mechanism may be used that enables filter 100 to be selectively positioned, captured, maintained in a relative position, and function as described herein. In another embodiment, filter 100 is coupled directly to a deployment and retrieval tool (not shown in FIG. 1 or 2), such as a catheter.

Figure 3:
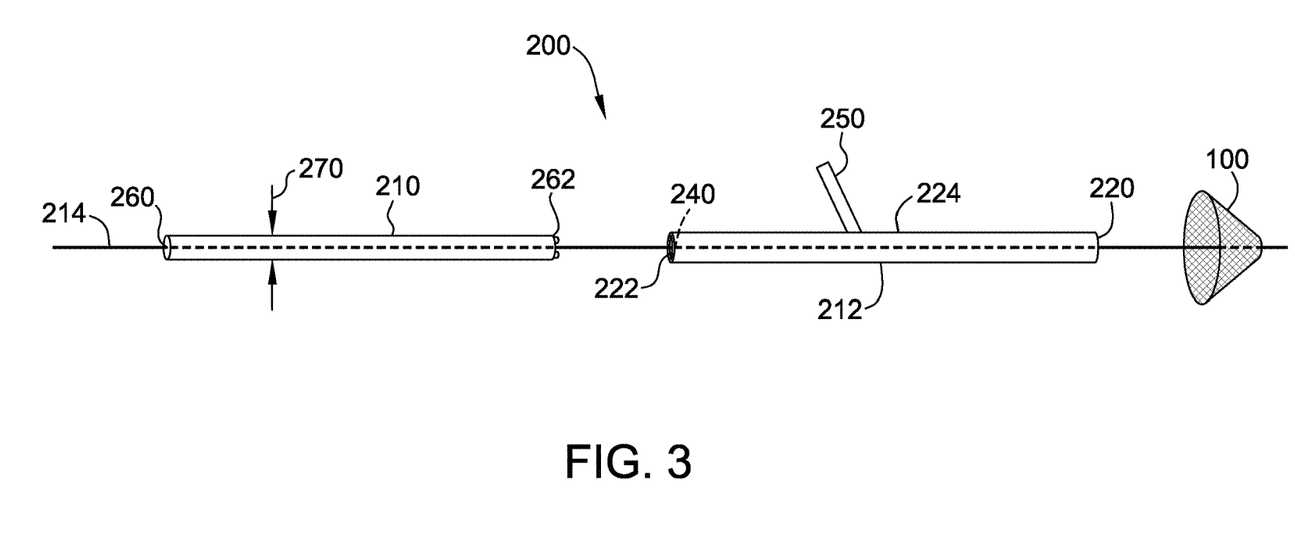
FIG. 3 is an exploded schematic view of an exemplary embolic filter delivery assembly for use in a transapical delivery approach with the filter shown in FIGS. 1 and 2.
Figure 4:
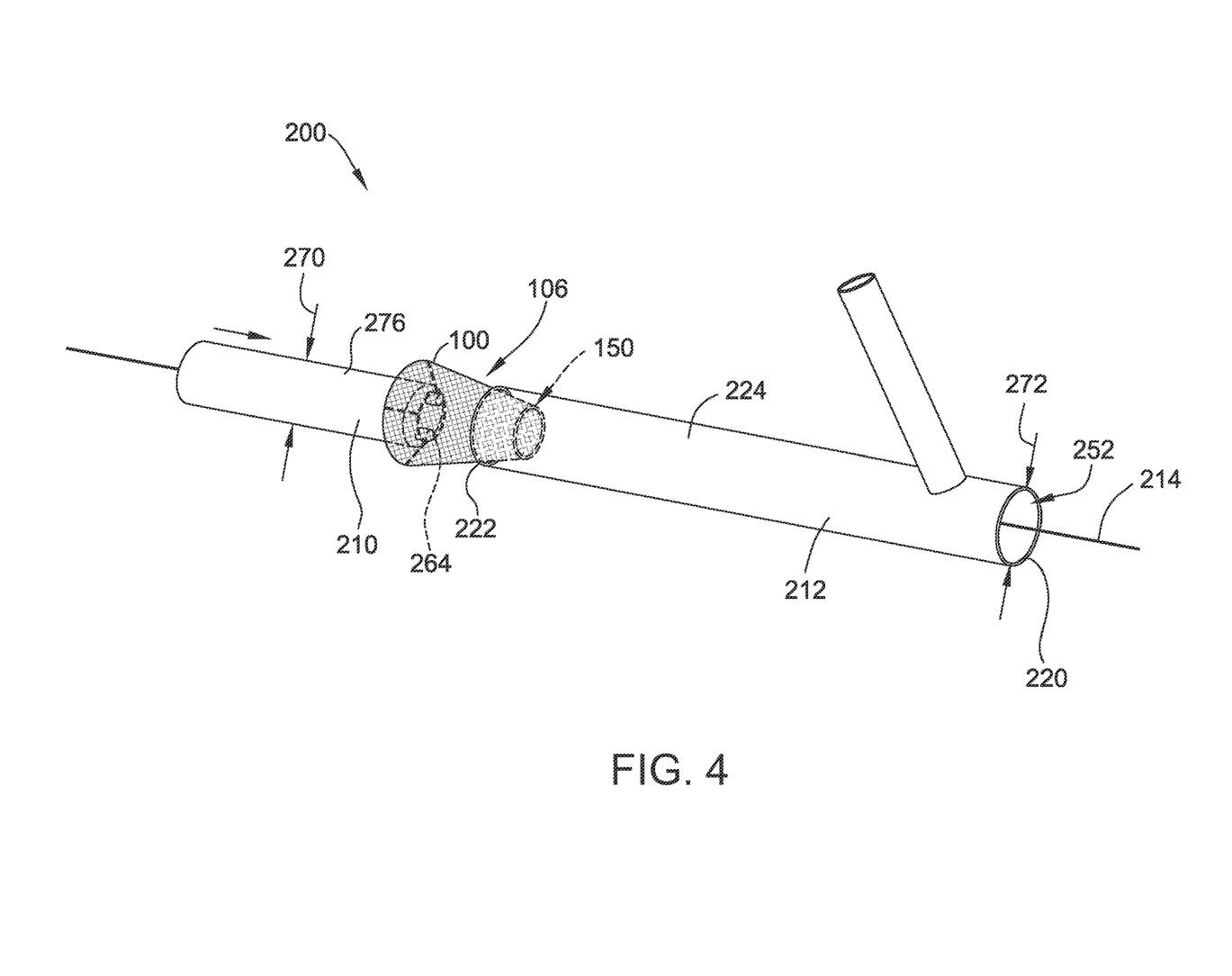
FIG. 4 is schematic perspective view of the filter delivery assembly shown in FIG. 4 including the filter shown in FIG. 2 being initially stored within the filter delivery system for insertion into a patient.

FIG. 3 is an exploded schematic view of an embolic filter delivery assembly 200 that may be used with filter 100. FIG. 4 is schematic view of filter delivery assembly 200 wherein filter 100 is being stored within filter delivery assembly 200 for insertion into a patient. In the exemplary embodiment, filter delivery assembly 200 includes a deployment and retrieval tool 210, a delivery sheath 212, and a guide wire 214. Sheath 212, in the exemplary embodiment, includes an inner end 220, an outer end 222, and an elongated tubular body 224 extending therebetween. Body 224 is hollow and is fabricated in a thin-walled construction that enables body 224 to be flexible and that enables body 224 to be formed with an external diameter that facilitates reducing an overall size of body 224 to enhance positioning of assembly 200 within a blood vessel by a surgeon or operator. For example, in one embodiment, body 224 is fabricated from a flexible thermoplastic material. Moreover, in the exemplary embodiment, body 224 has a circular cross-sectional profile that is sized to contain filter 100 therein, in a collapsed state 106, for delivery into and retrieval from a patient.

In the exemplary embodiment, body inner end 220 is open and body outer end 222 includes a control mechanism 240 therein that limits access into and from sheath 212 through outer end 222. More specifically, control mechanism 240 prevents flow through body 224 while providing limited access into sheath 212 through outer end 222, as described in more detail herein. For example, control mechanism 240 may be, but is not limited to being a check valve, a one-way valve, and/or or a diaphragm that limits access into body 224 through outer end 222 and that substantially prevents anything, such as blood and/or debris entering sheath 212 through inner end 220 from exiting sheath 212 through outer end 222. As such, in the exemplary embodiment, control mechanism 240 substantially prevents blood from entering or exiting sheath 212, and substantially prevents air from entering the patient's blood stream through sheath 212. Alternatively, any other control mechanism may be used that enables delivery assembly 200 to function as described herein.

Sheath 212 also includes a side port 250 that is in flow communication with the cavity 252 defined within sheath 212 and that enables selective aspirating of sheath 212. In particular, when filter assembly 200 is used with a non-transapical procedure, port 250 enables debris captured in filter 100 to be aspirated from sheath 212 for analysis without requiring any occlusion of blood flow.

Moreover, side port 250 enables selective aspirating of sheath 212 without requiring that sheath 212 be removed from the patient's blood vessel. Specifically, at times during use, sheath 212 will extend circumferentially about at least a portion of filter 100, a portion of guide wire 214, and at least a portion of deployment and retrieval tool 210. Side port 250 enables aspiration of sheath 212 while filter, guide wire 214, and tool 210 are contained at least partially within sheath 212.

In the exemplary embodiment, tool 210 is an elongated tube that includes a drive-control end 260 that provides deployment, positioning, and retrieval control to an operator during use of system 200, and a coupling end 262 that enables tool 210 to selectively couple to filter 100 during deployment, positioning, and retrieval of filter 100. More specifically, in the exemplary embodiment, coupling end 262 is formed with a socket-like projection 264 that enables end 262 to couple in a pre-defined orientation against at least a pair of support struts 134 on filter end 110. Moreover, coupling tool 210 to filter 100 facilitates accurately positioning filter 100 within a blood vessel, enables filter 100 to be retrieved from a blood vessel, and/or enables filter 100 to be selectively expanded within a blood vessel, as described in more detail below.

In the exemplary embodiment, tool 210 has an outer diameter 270 that is smaller than an inner diameter 272 of sheath 212. Moreover, tool 210 is sized and shaped, as defined by its outer surface 276, to be slideably coupled and rotatable within sheath 212. More specifically, tool 210 may be inserted into sheath 212 such that sheath control mechanism 240 is substantially circumferentially sealed against tool 210.

In the exemplary embodiment, assembly 200 is described in conjunction with a transapical delivery and guide wire 214 that extends through tool 210, through sheath 212, and through filter 100. More specifically, in the exemplary embodiment, guide wire 214 extends substantially concentrically through filter 100, from filter center coupling mechanism 132 through closed end 112. In one embodiment, in particular with non-transapical delivery methods, a device, such as guide wire 214, a catheter (not shown in FIG. 3 or 4), or any other deployment tool, may couple to filter closed end 112 to facilitate deployment and retrieval of filter 100. For example, in one embodiment, a portion of guide wire 214 or a catheter, for example, may be threadably coupled to a portion of filter closed end 112 as guide wire 214 is extended through and rotated within closed end 112. In another embodiment, guide wire 214 or a catheter, for example, is magnetically coupled to closed end coupling mechanism 150. In a further embodiment, guide wire 214 or a catheter, for example, is threadably coupled to coupling mechanism 150. Alternatively, any deployment and retrieval device, including guide wire 214 and/or a catheter, for example, may couple to filter 100 in any other means that enables assembly 200 to function as described herein. In the exemplary embodiment, the combination of filter support structure 126 and guide wire 214 enables filter 100 to be self-centered within the blood vessel when positioned in an expanded state 104 therein.

In the exemplary embodiment, delivery assembly 200 is intended for use with a transapical route of delivery into the patient while the patient's heart remains beating. During a transapical route of delivery, delivery system 200 is inserted into the patient through an incision created within the patient's chest (not shown) and below their heart. Assembly 200 is intended for use without cardiopulmonary bypass and does not generally require that a patient's chest or breastbone be opened beyond that incision, or that the patient use a heart-lung machine. Moreover, assembly 200 does not require any occlusion of blood flow or any inflatable components.

Initially, assembly 200 is prepared for delivery into a patient by initially storing filter 100 within delivery assembly 200 by folding or compressing filter 100 into a collapsed state 106 and storing filter 100 within sheath 212. More specifically, in the exemplary embodiment, the design of filter 100 enables it to be selectively and easily repositioned into its collapsed state 106 during use. More specifically, in the exemplary embodiment, a radially outer end 280 (shown in FIG. 1) of each strut 134 (shown in FIG. 1) is securely coupled to support ring 130 (shown in FIG. 1), and a radially inner end 282 of each strut 134 is hingedly or flexibly coupled to center coupling mechanism 132 (shown in FIG. 1). In an alternative embodiment, filter support structure 126 may have any other collapsible feature, orientation, geometry, or coupling arrangement that enables filter 100 to function as described herein. For example, in one embodiment, filter 100 includes a cinch that enables filter open end 110 to be selectively drawn closed.

For use in a surgical procedure wherein a transapical approach is being used, in the exemplary embodiment initially guide wire 214 is extended through tool 210, through filter 100 and through sheath 212. Although described herein in conjunction with a transapical delivery, assembly 200 and filter 100 may be used with transapical and/or arterial delivery approaches, such as a transfemoral delivery approach within a patient. As used herein, generally in a transapical approach, filter 100 is delivered through an incision in the patient's chest. Moreover, it should be noted that although generally described herein in association with a transfemoral delivery, arterial delivery approaches can be through any artery including radial or subclavian arteries, for example.

More specifically, in the exemplary embodiment, and with respect to filter 100, guide wire 214 extends substantially concentrically through filter open end 110, through filter body 114, and through closed end 112. Filter 100 is initially positioned, in its expanded state 104, adjacent to, or against sheath 212 such that filter closed end 112 is substantially concentrically aligned with, and is adjacent to or against, sheath outer end 222. Tool 210 is then positioned against filter 100 such that tool coupling end 262 contacts filter support structure 126 to enable filter 100 to be selectively collapsed into its collapsed state 106. More specifically, tool 210 is positioned such that tool projection 264 engages at least a portion of filter support structure 126 and more preferably at least one spoke 134.

Tool 210 is then advanced into filter open end 110 towards filter closed end 112. In the exemplary embodiment, because struts 134 are hingedly coupled to center coupling mechanism 132, struts 134 are folded back into the filter pocket defined by filter body 114. Concurrently, as struts 134 are folded back, support ring 130 is drawn inwardly towards centerline axis 153 such that filter open end diameter 120 is decreased smoothly and such that at least a portion of the flexible screen 144 is folded inwardly around and between struts 134. Moreover, because filter closed end diameter 122 is smaller than sheath inner diameter 272, as tool 210 is advanced against filter 100, filter closed end 112 is forced into sheath outer end 222. Eventually, the outer diameter 120 of filter 100, as defined at open end 110, is decreased to be smaller than sheath inner diameter 272 and filter 100 is forced into sheath 212 and through sheath control mechanism 240. Once stored in sheath cavity 252, sheath 212 extends circumferentially about filter 100, and about at least a portion of guide wire 214 and tool 210. More specifically, when stored for delivery in sheath 212, filter 100 is positioned between tool 210 and sheath inner end 220.

Delivery system 200 is then inserted into the patient and advanced through the patient's vasculature to a desired location. For example, in the exemplary embodiment, assembly 200 is advanced into the patient's aorta and is positioned downstream from an aortic valve undergoing the surgical procedure. To facilitate accurate placement of filter 100, the position of system 200 may be monitored using fluoroscopy or ultrasound, such as transesophageal echography (TEE), for example. Moreover, an appropriate marker, such as a radiopaque marker and/or a sonoreflective marker, may be coupled to a portion of system 200 to facilitate monitoring the position of assembly 200 and the deployment of filter 100.

After delivery assembly 200 has been advanced to a desired location within the blood vessel, tool 210 is longitudinally advanced within sheath 212 towards sheath inner end 220 such that filter 100 is forced outward from sheath cavity 252 along guide wire 214. Once released from sheath 212, the biasing of filter 100 enables filter 100 to be passively self-expanded within the blood vessel to its deployed state 104. More specially, when fully deployed, filter ring 130 is positioned substantially circumferentially against an inner wall of the blood vessel such that filter open end 110 extends substantially across the entire cross-section of the blood vessel and is substantially self-centered within the blood vessel. As such, substantially all of the blood flowing downstream from the surgical location enters filter open end 110 and flows through body screen 144. Moreover, because filter open end 110 is biased towards deployed state 104, filter open end 110, and more specifically, support ring 130 is passively and atraumatically positioned against and substantially conforms against the inner wall of the blood vessel such that at least some patient-to-patient variations in blood vessel diameter, such as aortic luminal diameter, are accommodated. In one embodiment, filter 100 includes a fastening mechanism, such as a mechanical component, that must be repositioned to enable filter 100 to expand to deployed state 104. Moreover, the conical shape of body 114 facilitates ensuring that the filter pocket defined by screen 144 remains a distance away from the blood vessel walls to prevent obstructing blood from flowing through filter pores 142.

After the surgical procedure is complete, in the exemplary embodiment, tool 210 is advanced from sheath 212 and against filter support structure 126. As filter diameter 120 is reduced, sheath 212 is repositioned around tool 210 and filter 100 such that filter 100 is returned into sheath cavity 252. More specifically, as sheath 212 is moved circumferentially about filter 100, any embolic materials captured by screen 144 remain within filter body 114 and the patient is protected from embolization during the surgical procedure. Moreover, after filter 100 has been moved back into sheath cavity 252, materials contained in filter body 114 may be selectively aspirated for analysis from sheath 212 via port 250.

Figure 5:
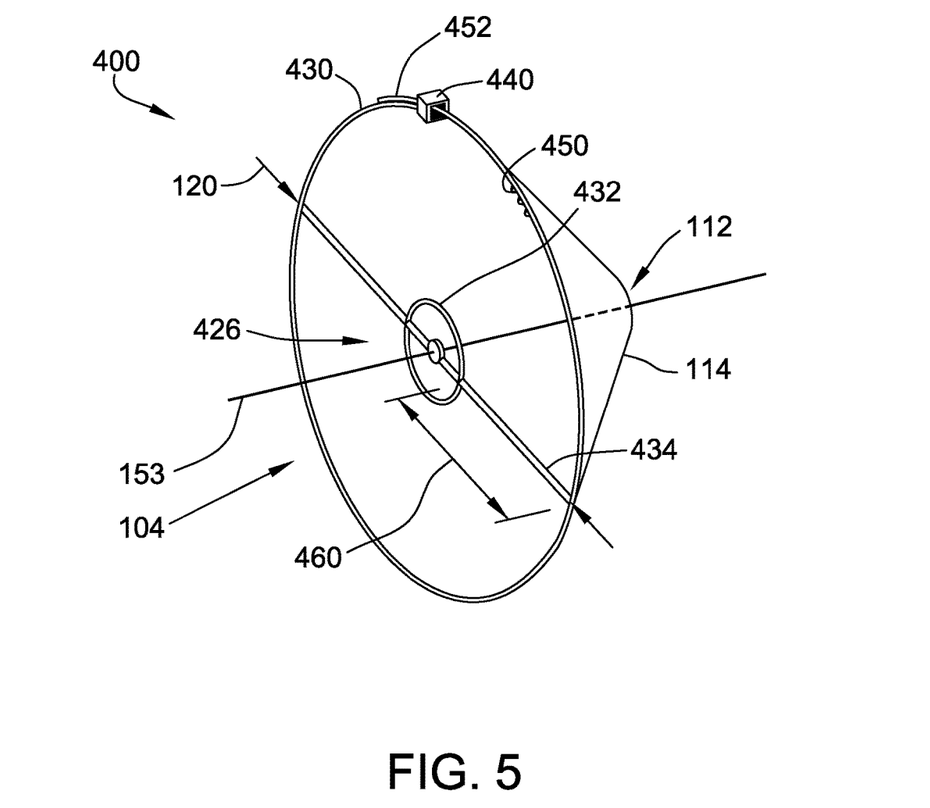
FIG. 5 is an alternative filter that may be used with the filter assembly shown in FIGS. 3 and 4.

FIG. 5 is an alternative filter 400 that may be used with the filter delivery assembly shown in FIGS. 3 and 4. Filter 400 is substantially similar to filter 100 (shown in FIGS. 1 and 2) and components of filter 400 that are identical to components used with filter 100 are identified in FIG. 5 using the same reference numbers used in FIGS. 1 and 2. Accordingly, in the exemplary embodiment, filter 400 functions similarly to filter 100 and includes open end 110, filter body 114, and closed end 112. Filter 400 also includes a support structure 426 that biases filter 400 towards expanded state 104 and that filter 100 to be selectively transitioned from deployed state 104 to collapsed state 106.

In the exemplary embodiment, filter support structure 426 includes a split support ring 430, a center coupling mechanism 432, and a plurality of telescoping or compressible struts 434, that work in combination to provide support to filter body 114 at open end 110 and to provide a means to selectively transition filter 400 from deployed state 104 to collapsed state 106. In one embodiment, ring 430 is formed in a split ring configuration that includes an adjustment mechanism 440 that enables an operator to selectively adjust a diameter 120 of open end 110 after filter 100 is deployed in a desired location within a blood vessel. More specifically, in the exemplary embodiment, ring 430 includes a plurality of teeth 450 (only three are shown for clarity) that engage a portion of adjustment mechanism 440 as a portion 452 of ring 430 is pulled or pushed through adjustment mechanism 440. Moreover, as ring portion 452 is drawn through mechanism 440, filter open end diameter 120 is reduced and a length 460 of each spoke 434 is selectively reduced. In one embodiment, ring portion 452 is drawn through mechanism 440, as tool 210 is rotated after engaging struts 434. In such an embodiment, to facilitate adjustments to filter open end diameter 120, a portion of filter body screen 144 overlaps itself, such that as open end diameter 120 is adjusted, no gaps are created within filter body screen 144.

Figure 6:
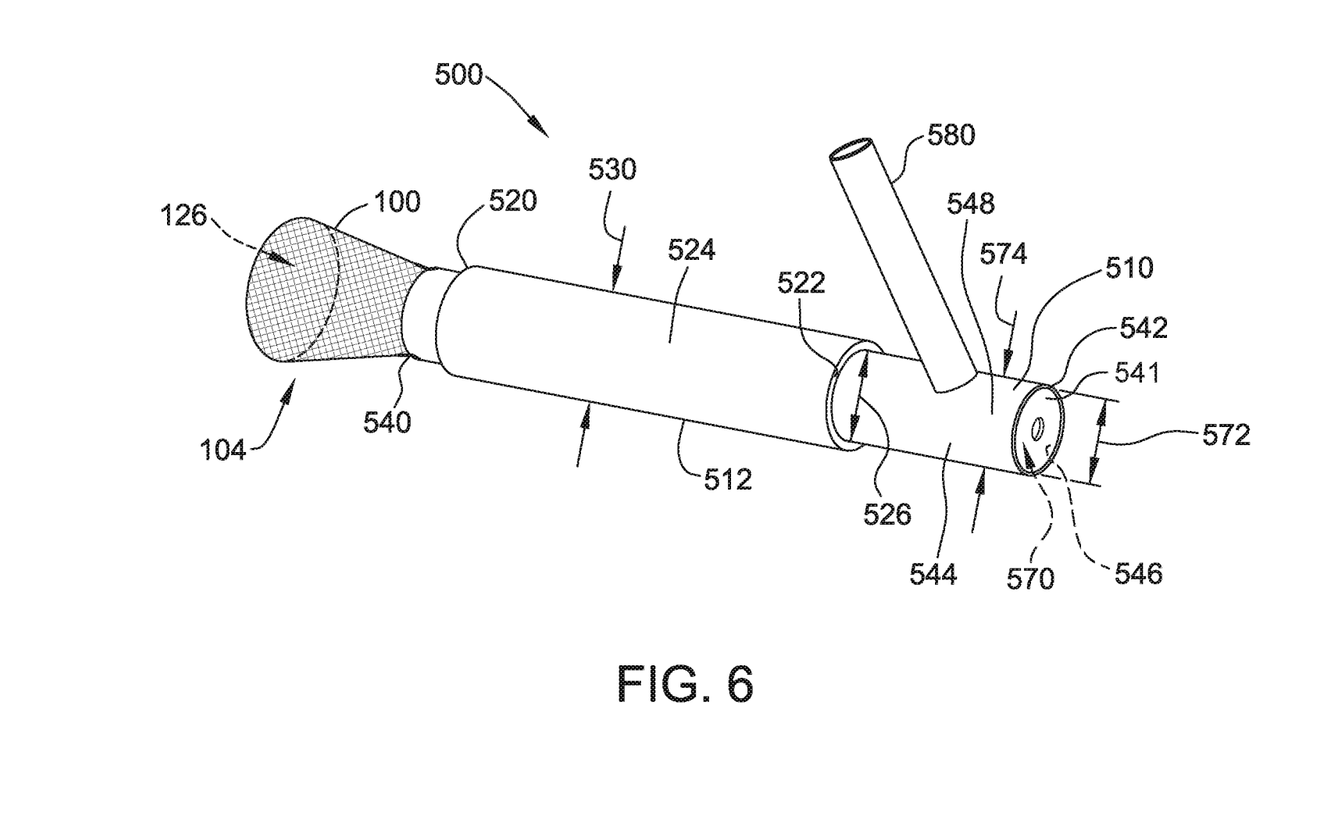
FIG. 6 is a schematic perspective view of an alternative embolic filter delivery assembly for use in a non-transapical delivery approach with the filter shown in FIGS. 1 and 2, for example.

FIG. 6 is a schematic perspective view of an alternative embolic filter delivery assembly 500 for use in a non-transapical delivery approach with embolic capture device 100. Delivery assembly 500 functions similarly to delivery assembly 200 (described above with respect to FIGS. 3 and 4) and identical components are identified in FIG. 6 using the same reference numbers used in FIGS. 3 and 4. Accordingly, in the exemplary embodiment, delivery assembly 500 includes a deployment and retrieval tool 510, and a sheath 512. In alternative embodiments, delivery assembly 500 may also include a guide wire. Sheath 512, in the exemplary embodiment, includes an inner end 520, an outer end 522, and an elongated tubular body 524 extending therebetween. Body 524 is hollow and is fabricated in a thin-walled construction that enables body 524 to be flexible and that enables body 524 to be formed with an external diameter 530 that facilitates reducing an overall size of body 524 to enhance positioning of assembly 500 within a blood vessel by a surgeon or operator. For example, in one embodiment, body 524 is fabricated from a flexible thermoplastic material. Moreover, in the exemplary embodiment, body 524 has a circular cross-sectional profile that is sized to contain at least a portion of deployment tool 510 (i.e., sized to enable body 524 to extend substantially circumferentially about a portion of tool 510), and filter 100 therein, in a collapsed state 106, for delivery into, and retrieval from, a patient. In the exemplary embodiment, body inner and outer ends 520 and 522 are each open and each is sized with approximately the same inner diameter 526. More specifically, in the exemplary embodiment, the cavity defined within sheath 512 is defined by a substantially constant diameter 526 that is sized to contain at least a portion of tool 510 and filter 100 therein, in a collapsed state 106, for delivery into, and retrieval from, a patient.

In the exemplary embodiment, deployment and retrieval tool 510 is a hollow catheter that may be pre-formed with any shape, such as an arcuate shape, that facilitates its use in the cardiac surgery. In alternative embodiments, any other deployment and retrieval tool may be used that enables assembly 500 to function as described herein, such as a central lumen, for example. For example, in one embodiment, tool 510 may be a catheter that has been formed with a curve that facilitates accommodating use of the tool in a patient's aortic arch. Tool 510 includes an inner end 540, an outer end 542, and an elongated tubular body 544 extending therebetween. Body 544 is hollow and is fabricated in a thin-walled construction that enables body 544. Moreover, in the exemplary embodiment, body 544 has a substantially circular inner cross-sectional profile defined by an inner wall surface 546, and a substantially circular outer profile defined by an external wall surface 548. In the exemplary embodiment, inner wall surface 546 defines a cavity 570. Furthermore, body external surface 548 defines a substantially circular outer profile that has a diameter 574 that is sized and shaped to enable tool 510 to be slidably and rotatably coupled within sheath 512.

In the exemplary embodiment, tool outer end 542 includes a control mechanism 541 therein that limits access into and from tool 510 through outer end 542. More specifically, in the exemplary embodiment, the control mechanism 541 prevents flow through tool 510 while limiting access into tool 510 through outer end 542, as described in more detail herein. For example, the control mechanism 541 may be, but is not limited to being a check valve, a one-way valve, and/or or a diaphragm that limits access into tool 510 through outer end 542 and that substantially prevents anything, such as blood and/or debris entering sheath tool 510 through inner end 520 from exiting tool 510 through outer end 542. As such, in the exemplary embodiment, the control mechanism 541 substantially prevents blood from exiting tool 510, and substantially prevents air from entering the patient's blood stream through sheath 512. Alternatively, any other control mechanism may be used that enables delivery assembly 500 to function as described herein.

Tool 510, in the exemplary embodiment, also includes a side port 580 that is in flow communication with the cavity 546 defined within tool 510 and that enables selective aspirating of tool 510. In particular, when filter assembly 500 is used with a non-transapical procedure, port 580 enables debris captured in filter 100 to be aspirated from tool 510 for analysis and to enable any debris captured within filter 100 or within tool 510 to be safely removed from the patient, without requiring any occlusion of blood flow. Moreover, side port 580 enables selective aspirating of tool 510 without requiring that tool 510 be removed from the patient's blood vessel. In alternative embodiments, tool 510 may include more than one port 580 or may not include any ports 580. Specifically, at times during use, sheath 512 will extend circumferentially about at least a portion of filter 100, and at least a portion of deployment and retrieval tool 510, and port 580 enables aspiration of tool 510 and filter 100, while filter 100 is contained therein and while tool 510 and filter 100 are at least partially contained within sheath 512.

In the exemplary embodiment, assembly 500 is intended for use with filter 100 and is coupled to filter 100 for use in a non-transapical delivery. More specifically, in the exemplary embodiment, tool inner end 540 is coupled to filter end 112 (shown in FIG. 1). More specifically, in the exemplary embodiment, filter end 112 is coupled to tool inner wall surface 546 within cavity 570. For example, in one embodiment, tool inner end 540 is magnetically coupled to filter coupling mechanism 150 (shown in FIG. 1) within cavity 570 or such that filter 100 sealing mates against tool inner end 540. In another embodiment, tool inner end 540 is threadably coupled to filter coupling mechanism 150 and/or filter end 112 such that filter end 112 is either within cavity 570 or sealingly mates against tool inner end 540. Alternatively, filter end 112 may be coupled against tool inner end 540 or coupled substantially circumferentially coupled to surface 546 within cavity 570 using any other coupling mechanism that enables assembly 500 to function as described herein, such as, but not limited to mechanical coupling mechanisms, RF welding, magnetic coupling, and/or chemical bonding, for example.

In the exemplary embodiment, filter 100 extends from tool 510 and is biased to its open configuration 104. Moreover, in the exemplary embodiment, filter 100 includes at least a portion of support structure 126, and more specifically, includes only ring 130 and does not include any struts 134 (shown in FIGS. 1 and 2). In another embodiment, filter 100 does not include ring 130 and rather filter body 114 biases filter 100 to deployed state 104. In other embodiments, to facilitate retrieval of filter 100, and/or to facilitate filter 100 transitioning from expanded state 104 to collapsed state 106, a portion of filter 100, such as filter body 114

(shown in FIGS. 1 and 2) may be hingedly coupled to tool 510. In the exemplary embodiment, the combination of filter support structure 120 and the coupling to tool 510 enables filter 100 to be self-centered within the blood vessel when positioned in an expanded state 104 therein.

In the exemplary embodiment, delivery assembly 500 is described in conjunction with a non-transapical (i.e., an arterial) delivery into the patient and additional tools and/or surgical devices, such as a pigtail catheter, other catheters, and/or other surgical components, such as a replacement aortic valve, for example, that may be needed for use with the surgical procedure. Filter 100 is configured to accommodate the use of additional tools and/or surgical components, and in the exemplary embodiment, such tools and/or surgical components may be passed or moved through tool 510 and through the tool control mechanism, and subsequently through filter 100 and upstream to the surgical procedure location. Specifically, in procedures in which additional tools, such as a guide wire or catheter-based instrument, for example, may be needed, filter end 112 may be pre-formed with an opening or access (not shown) that enables such tools and/or surgical components to be delivered via an arterial delivery through assembly 500, and more specifically, through tool 510, to the surgical procedure location. During such procedures, blood will still be filtered via screen 144 and any blood and/or debris entering tool 510 through the opening formed in filter end 112 may be aspirated as necessary. Moreover, during such procedures, the control mechanism within tool 510 substantially prevents flow through tool 510 while providing limited access into tool 510 and through filter 100. For example, such a control mechanism may be, but is not limited to being a check valve, a one-way valve, and/or or a diaphragm that limits access, including air ingress, into tool cavity 546 through tool outer end 542, and that substantially prevents anything, such as blood and/or debris that enters filter 100 and/or tool 510 from exiting cavity 546 through outer end 542. Any other control mechanism may be used that enables delivery assembly 500 to function as described herein.

In the exemplary embodiment, delivery system 500 is intended for use with an arterial route of delivery into the patient. During an arterial route of delivery, delivery assembly 500 is inserted into the patient through their vasculature, such as their femoral artery, remote from the patient's heart. Assembly 500 is intended for use without cardiopulmonary bypass. Moreover, system 500 does not require any occlusion of blood flow or any inflatable components.

Initially, assembly 500 is prepared for insertion within a patient by folding or compressing filter 100 into a collapsed state 106 and storing filter 100 and tool 510 within sheath 512. More specifically, in the exemplary embodiment, the design of filter 100 enables it to be selectively and easily repositioned into its collapsed state 106 during use. For use in a surgical procedure, when assembly 500 is positioned at a desired location within the blood vessel, in the exemplary embodiment, as sheath 512 is selectively moved, relative to tool 510, towards tool end 542, filter is deployed into its expanded state 104, such that filter 100 remains coupled to and substantially concentrically aligned with tool 510. More specifically, in one embodiment, after delivery assembly 500 has been advanced to a desired location within the blood vessel, sheath 512 is held in a relatively constant position, and tool 510 is advanced outward from sheath end 520 such that filter 100 is sprung outward from the sheath cavity while remaining coupled to tool 510. In another embodiment, after delivery system 500 has been advanced to a desired location within the blood vessel, tool 510 is held in a relatively constant position, and sheath 512 is moved relative to tool 510 such that filter 100 is sprung outward from the sheath cavity while remaining coupled to tool 510.

Once released from sheath 512, the biasing of filter 100 enables filter 100 to be passively self-expanded within the blood vessel to its deployed state 104 while remaining coupled to tool 510. More specially, when fully deployed, filter ring 130 is positioned substantially circumferentially against an inner wall of the blood vessel and is self-centered within the blood vessel such that filter open end 110 extends substantially across the entire cross-section of the blood vessel. As such, substantially all of the blood flowing downstream from the surgical location enters filter open end 110 and flows through body screen 144. Moreover, because filter open end 110 is biased towards deployed state 104, filter open end 110, and more specifically, support ring 130 is passively and atraumatically positioned against the inner wall of the blood vessel such that at least some patient-to-patient variations in blood vessel diameter, such as aortic luminal diameter, are accommodated. Moreover, the conical shape of body 114 facilitates ensuring that the filter pocket defined by screen 144 remains a distance away from the blood vessel walls to prevent obstructing blood from flowing through filter pores 142.

After the surgical procedure is complete, in the exemplary embodiment, sheath 512 is selectively advanced towards filter 100 along tool 510 until against filter 100. As sheath 512 is advanced upstream towards filter open end 110 and along tool 510, filter diameter 120 (shown in FIG. 1) is reduced, and tool 510 and filter 100 may be repositioned within the sheath cavity. In one embodiment, during the retrieval process, tool 510 is held in a substantially constant position relative to the blood vessel, and sheath 512 is moved along tool 510 and towards filter 100 until filter 100 is positioned within the sheath cavity. In another embodiment, during the retrieval process, sheath 512 may be held in a substantially constant position relative to the blood vessel, and tool 510 and filter 100 may be drawn into the sheath cavity. More specifically, in each embodiment, during the retrieval, as sheath 512 is moved circumferentially around filter 100, any embolic materials captured by screen 144 remain within filter body 114 and the patient is protected from embolization during the surgical procedure. Moreover, after filter 100 has been moved back into the sheath cavity, materials contained in filter body 114 may be selectively aspirated for analysis from tool 510 via port 580. In one embodiment, tool 510 may include a mechanical mechanism that may be rotated to facilitate transitioning filter 100 to its collapsed state 106.

The above-described embolic filter delivery systems provide a user with enhanced flexibility in delivery options and an enhanced positioning and deployment control. Moreover, in some embodiments, the above-described filter delivery system enables an operator to deliver additional instruments or devices in a delivery path through the embolic capture device, in a manner that maintains the filtering of the patient's blood stream despite the instruments being delivered and/or retrieved through the filter. As compared to known embolic filtrations systems, the filtration systems described herein are simpler in design, are less complicated to use, and are more reliable. The filters described herein are easily deployable and retrievable and advantageously do not require the use of cardiopulmonary bypass, flow occlusion, or inflation of any component, such that risks to the patient are facilitated to be reduced as compared to known filtering systems. Moreover, the filters described herein are self-centering within a blood vessel and as such are more accurately positioned than known filtering systems. As a result, a filter assembly is provided which facilitates decreasing the risks, including the risks of a stroke, to the patient in a cost-effective and highly reliable manner.

Exemplary embodiments of methods and fastener mechanisms for use in capturing embolic debris during surgical procedures are described above in detail. Although the methods are herein described and illustrated in association with the above-described filter and delivery system, it should be understood that the present invention may be used with any filter and/or delivery system. More specifically, the filters, delivery systems, and methods of capturing embolic debris are not limited to the specific embodiments described herein, but rather, aspects of each filter, delivery system, and/or method of capture may be utilized independently and separately from other filter, delivery system, and/or capture method.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An embolic protection system for use in capturing embolic debris entrained within blood flowing along a blood vessel of a patient at a desired location that is downstream of a location at which an endovascular procedure is to be performed using a surgical component, said embolic protection system comprising:
    a filter having a first end and a second end, wherein said second end defines an inlet opening and said first end defines an access opening;
    a filter delivery system coupled to said filter for delivery of said filter along the blood vessel to the desired location via an arterial approach, wherein said filter delivery system comprises:
        a sheath comprising a hollow sheath body that extends from an open sheath proximal end to an open sheath distal end and defines an internal sheath cavity therebetween, said open sheath ends and said internal sheath cavity defined by an inner surface of said sheath body and having a same, substantially constant inner diameter, wherein said sheath body extends continuously between said open sheath ends; and
        a hollow deployment tool comprising a hollow tool body that extends from a tool proximal end to an open tool distal end, wherein an outer surface of said deployment tool is slidably coupled to said inner surface of said sheath body such that a seal is defined therebetween, said deployment tool defining an internal tool cavity that extends from said tool distal end to said tool proximal end, said open tool distal end coupled to said filter first end; and
        a control mechanism coupled to said deployment tool proximal end, said control mechanism substantially prevents blood from exiting said tool cavity at said proximal end of said deployment tool, wherein when said filter is deployed at the desired location in the patient, (i) said filter second end defines a distal-most location of said embolic protection system, and (ii) said embolic protection system is adapted to pass the surgical component therethrough through said control mechanism, through said tool proximal end, through said sheath proximal end, through said sheath distal end, through said open tool distal end, and through said filter via said access opening and said inlet opening upstream to the location of the endovascular procedure.

2. An embolic protection system in accordance with claim 1 wherein said sheath extends circumferentially about said deployment tool and said filter when said filter is being at least one of delivered to the desired location and retrieved from the desired location.

3. An embolic protection system in accordance with claim 1 wherein said hollow deployment tool further comprises a port that facilitates selective aspiration of said filter.

4. An embolic protection system in accordance with claim 1 wherein said filter is self-expanding when deployed.

5. An embolic protection system in accordance with claim 1 wherein said filter is self-centering within the blood vessel when deployed.

6. An embolic protection system in accordance with claim 1 wherein said filter is selectively moveable from a collapsed state to an expanded state.

7. An embolic protection system in accordance with claim 1 wherein said deployment tool is slidable within said sheath to:
    selectively release said filter from said sheath; and
    selectively reposition said filter within said sheath.

8. An embolic protection system in accordance with claim 1 wherein said filter is removable from the blood vessel after the endovascular procedure.

9. A method of capturing embolic debris entrained within blood flowing along a blood vessel, said method comprising:
    delivering a filter along the blood vessel to a desired filter location via an arterial approach using a filter delivery system, the filter having a first end and a second end, wherein the second end defines an inlet opening and the first end defines an access opening, and wherein the filter delivery system includes:
        a sheath including a hollow sheath body that extends from an open sheath proximal end to an open sheath distal end and defines an internal sheath cavity therebetween, the open sheath ends and the internal sheath cavity defined by an inner surface of the sheath body and having a same, substantially constant inner diameter, wherein the sheath body extends continuously between the open sheath ends,
        a hollow deployment tool comprising a hollow tool body that extends from a tool proximal end to an open tool distal end, wherein an outer surface of the deployment tool is slidably coupled to the inner surface of the sheath body such that a seal is defined therebetween, the deployment tool defining an internal tool cavity that extends from the tool distal end to the tool proximal end, the open tool distal end coupled to the filter first end, and
        a control mechanism coupled to the deployment tool proximal end, wherein the control mechanism substantially prevents blood from exiting the cavity at the proximal end of the deployment tool;

deploying the filter at the desired filter location in the patient such that the filter second end defines a distal-most location of the filter delivery system; and passing a surgical component through the control mechanism, through the tool proximal end, through the sheath proximal end, through the sheath distal end, through the open tool distal end, and through the filter via the access opening and the inlet opening upstream to a location of an endovascular procedure to be performed using the surgical component.

10. A method in accordance with claim 9, further comprising retaining the filter within a circumferential extent of the deployment tool during the step of delivering the filter.

11. A method in accordance with claim 9, further comprising selectively aspirating the filter via a port defined in the hollow deployment tool.

12. A method in accordance with claim 9, wherein the step of deploying the filter comprises allowing the filter to self-expand.

13. A method in accordance with claim 9, wherein the step of deploying the filter comprises allowing the filter to self-center within the blood vessel.

14. A method in accordance with claim 9, wherein the step of deploying the filter comprises the filter moving from a collapsed state to an expanded state.

15. A method in accordance with claim 9, wherein the step of deploying the filter comprises sliding the deployment tool within the sheath to selectively release the filter from the sheath.

16. A method in accordance with claim 9, further comprising sliding the deployment tool within the sheath to selectively reposition the filter within the sheath after the endovascular procedure is completed.

17. A method in accordance with claim 9, further comprising removing the filter from the blood vessel after the endovascular procedure.

* * * * *